United States Patent [19]

Oliver-Shaffer et al.

[11] Patent Number: 5,801,250
[45] Date of Patent: Sep. 1, 1998

[54] PROCESS FOR THE STEREOSELECTIVE PRODUCTION OF NITRO-ENAMINE COMPOUNDS

[75] Inventors: Patricia A. Oliver-Shaffer, Lindenhurst; Bikshandarkoil A. Narayanan, Mundelein; James E. Resek, Lake Bluff; Pulla Reddy Singam, Chicago, all of Ill.

[73] Assignee: Abbott Laboratories, Abbott Park, Ill.

[21] Appl. No.: 764,866

[22] Filed: Dec. 13, 1996

[51] Int. Cl.$^6$ .................. C07D 405/04; C07D 317/60
[52] U.S. Cl. ........................... 548/526; 549/444
[58] Field of Search ..................... 549/444; 548/526

[56] References Cited

FOREIGN PATENT DOCUMENTS

WO 96/06095  2/1996  WIPO.

OTHER PUBLICATIONS

Grant et al., Grant & Hackh's Chemical Dictionary, 5th Ed., McGraw–Hill Book Company, New York, 1987, p. 453.
d'Angelo, J., et al., "A New Strategy for the Enantioselective Synthesis of Aspidosperma Alkaloids: I–Construction of the [ABC]–Type Tricyclic Intermediates", *Unit''de Chimie Organique Associée au CNRS*, 879–882 (1989).
d'Angelo, J., et al., "The Asymmetric Michael Addition Reactions Using Chiral Imines", *Tetrahedron: Asymmetry*, 3(4):459–505 (1992).
Desmaële, D., et al., "The Asymmetric Michael Reaction Involving Chiral Imines: Use of Acrylonitrile as Acceptor and Subsequent Functionalization of the Adducts", *Tetrahedron: Asymmetry*, 5(9):1645–1648 (1994).
Felk, A., et al., "Enantioselective Michael–type Reaction of Chiral Linear α,α–Disubstituted Secondary Enamines", *Tetrahedron: Asymmetry*, 5(8):1459–1462 (1994).
Pfau, M., et al., "Enantioselective Synthesis of Quaternary Carbon Centers through Michael–Type Alkylation of Chiral Imines", *American Chemical Society*, 107:273–274 (1985).
Pfau, M., et al., "Imine–Enamine Tautomerism–VI$^a$ C–vs N–Alkylation of Imines with Electrophilic Olefins", *Tetrahedron*, 35(15) 1899–1904 (1979).
Sevin, A., et al., "Toward a Transition–State Model in the Asymmetric Alkylation of Chiral Ketone Secondary Enamines by Electron–Deficient Alkenes. A Theoretical MO Study", *American Chemical Society*, 51(14):2671–2675 (1986).

*Primary Examiner*—Johann Richter
*Assistant Examiner*—Laura L. Stockton
*Attorney, Agent, or Firm*—Michael J. Ward

[57] ABSTRACT

The present invention relates to an asymmetric Michael Addition reaction to produce nitro ketone diasteroisomers with enhanced stereoselectivity.

19 Claims, No Drawings

PROCESS FOR THE STEREOSELECTIVE PRODUCTION OF NITRO-ENAMINE COMPOUNDS

FIELD OF THE INVENTION

The present invention involves an asymmetric Michael Addition reaction wherein a chiral enamino-ester isomer is used to produce nitro ketone diasteroisomers wherein stereoselectivity of particular diasteroisomers is enhanced.

BACKGROUND OF THE INVENTION

High yields of enatiomerically enriched α-disubstituted cyclanones have been produced by an efficient Michael process of reacting 1-phenylethylamine and an α-substituted cyclanone to produce a chiral imine which is then used to produce α-disubstituted cyclanones. *A New Strategy For The Enantioselective Synthesis Of Aspodosperma Alkaloids: I- Construction Of The [ABC]-Type Tricyclic Intermediates.* J. D'Angelo and D. Desmaële, Unite De Chimie Organique Associate au CNRS, pp879–882.

A limitation to imine production in linear carbonyl compounds is that both E and Z secondary enamine tautomers are formed. 2-Acetylbutyrolactone was reacted with (S)-2-methylbenzylamine to produce a single secondary enamine tautomer. *Enantioselective Michael-type Reaction of Chiral Linear α,α-Disubstituted Secondary Enamines.* A. Felk et al., Tetrahedron: Asymmetry, Vol. 5, No. 8, pp1459–1462, 1994.

There continues to be a need for processes involving asymmetric Michael Addition of chiral enamino-ester isomers with electron deficient olefins which produce diastereomers showing enhanced stereoselectivity.

The compounds made with the process of the present invention may be used in the process of making endothelin antagonist compounds, which have vasoactive properties. In particular, the process of the present invention may be useful in preparing compounds disclosed in PCT publication WO 96/06095, which was published Feb. 29, 1996. PCT publication WO 96/06095 is hereby incorporated by reference.

DETAILED DESCRIPTION OF THE INVENTION

A novel process of the present invention involves the asymmetric Michael Addition wherein a chiral enamino-ester isomer is used to produce nitro ketone diasteroisomers of enhanced diastereoselectivity. The process, as shown in Scheme 1, involves reacting a chiral primary amine compound (2) with a β-ketoester compound (1) to form a chiral enamino-ester (3). The chiral enamino-ester (3) is then reacted with a nitrostyrene compound (4) to form a chiral nitro enamine (5) in which one of the diastereomers produced is enhanced over the other. Hydrolysis of the chiral nitro enamine (5) results in formation of four nitro ketone (6) diastereomer products wherein two of the diastereomers are produced in greater quantities.

A preferred embodiment of the present invention as shown in Scheme 1 is the process wherein a chiral primary amine compound (2) may be reacted with a β-ketoester (1) in the presence of a first solvent and an acid to form a chiral enamino-ester (3). First solvents suitable for the reaction of the primary amine with the β-ketoester include, but are not intended to be limited to, tetrahydrofuran (THF), toluene, methyl tert-butyl ether (MTBE), and the like. The formation of the chiral enamino-ester (3) occurs over a period of several hours to several days. Alternatively, the reaction mixture may be refluxed for several hours.

A chiral primary amine compound suitable for the present invention includes primary amines wherein $R_1$ and $R_2$ are independently selected from the group consisting of alkyl, substituted and unsubstituted aryl, heterocyclic, and alkoxy. $R_3$ is selected from the group consisting of alkyl and substituted and unsubstituted aryl. A (S)-primary amine is used to produce a (S) enamino-ester and a (R)-primary amine is used to produce a (R) enamino-ester.

Ketoesters suitable with the present invention include β-ketoesters wherein $R_3$ is selected from the group of alkyl, and substitued and unsubstitued aryl.

The chiral enamino-ester (3) is formed by adding an acid to the primary amine/β-ketoester/first solvent mixture. Examples of suitable acids include, but are not intended to be limited to, acetic, citric, aspartic, benzoic, lactic, sulphuric, and succinic acids, and the like. The acid may be used in the range of from about 0.05 to about 1 equivalents of acid.

The chiral enamino-ester (3) is then reacted with a nitrostyrene compound (4) to form a nitro enamine (5). The nitro enamine (5) is then hydrolyzed to produce a nitro ketone (6). The chiral enamino-ester/nitrostyrene reaction to produce a nitro enamine may be carried out at a temperature range of from about −15° C. to about 100° C. A more preferred temperature range for the reaction is from about ambient temperature to about 70° C.

In another embodiment of the present invention, the chiral enamino-ester may be reacted with nitrostyrene to form a nitro enamine in the presence of a second solvent.

Second solvents suitable for reacting the enamino-ester with nitrostyrene include, but are not intended to be limited to, tetrahydrofuran (THF), acetonitrile, methyl tertbutyl ether (MTBE), toluene, ethyl acetate, alkanols including but not intended to be limited to, methanol, ethanol, and isopropanol, and the like. The reaction may be carried out at a temperature of from about −15° C. to the reflux temperature of the solvent. For example, alkanols may be used at room temperature for a period of several hours to several days to form the nitro enamine (5). Alternatively, the reaction may be done by refluxing the mixture at the particular alkanols reflux temperature for several hours.

A base may be used to help the reaction of the enaminoester (3) with nitrostyrene (4) in the presence of a second solvent to form the nitro enamine (5). Suitable bases for use in the reaction include, but are not intended to be limited to sodium ethoxide and potassium carbonate. The base may be used in the range of from about 0.05 to about 1 equivalents of base. Either (S) or (R) α-methyl benzylamine may be used to form the corresponding (S) or (R) ethyl(4-methoxyphenyl)-1-(αmethyl benzylamino) propionate (3).

Hydrolysis of the nitro enamine (5) to the nitro ketone (6) may be performed using an aqueous organic or an aqueous inorganic acid. Examples of suitable organic acids include, but are not intended to be limited to, acetic acid, citric acid, aspartic acid, benzoic acid, lactic acid, and succinic acid. Examples of suitable inorganic acids include, but are not intended to be limited to, hydrochloric acid, nitric acid, phosphoric acid, and sulfuric acid, Hydrogenation of the nitro enamines (5) to the imino pyrolidine (7) may be performed under hydrogenating conditions. For example, an acid solution (from about 0.01 to about 1 equivalents of an acid) containing the nitro enamines (5) and hydrogen in the presence of a catalyst results in the formation of the imino pyrolidine. Further hydrogenation of the imino pyrolidine may result in the formation of a pyrolidine compound (8).

Catalysts suitable for the present invention include, but are not intended to be limited to, Raney nickel, platinum, and palladium catalysts. The palladium catalysts may be palladium/carbon (Pd/C), palladium hydroxide (Pd(OH)$_2$, palladium (black), and palladium supported. Preferably, the palladium hydrogenation catalyst is Pd(OH)$_2$ or Pd/C.

The hydrogenation reaction to be carried out at a pressure from about 5 psi to about 100 psi. More preferably, the novel process of the present invention allows the hydrogenation reaction to be carried out at a pressure from about 5 psi to about 60 psi. The hydrogenation reaction may be performed at a temperature from about 5° C. to about 70° C. More preferably, the hydrogenation reaction is carried out at a temperature from about 60° C.

SCHEME 1

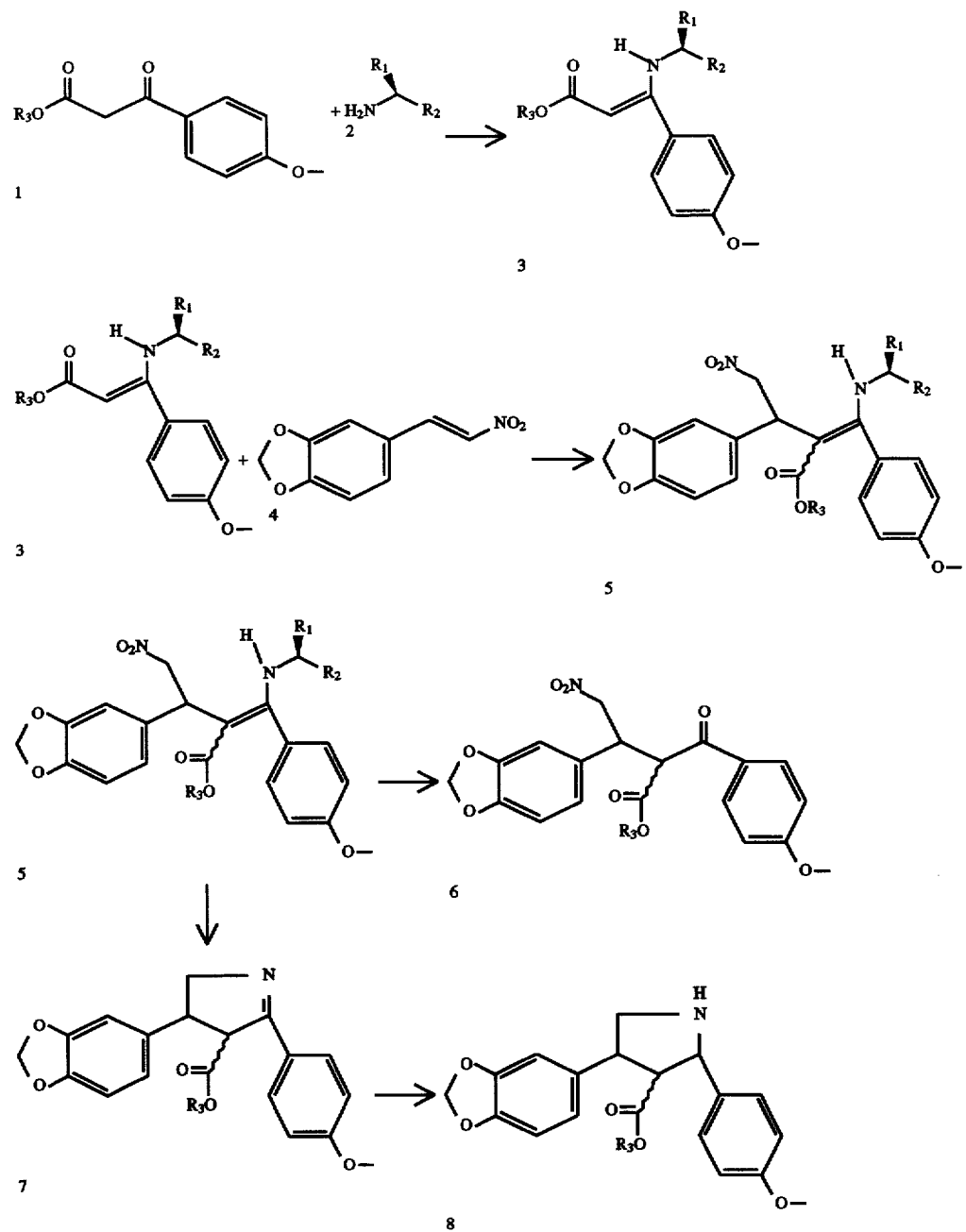

A more preferred embodiment is shown in Scheme 2. Scheme 2 involves reacting a chiral α-methyl benzylamine ((S) α-methyl benzylamine is shown in Scheme 2) with ethyl(4-methoxyphenyl)-1-oxo-proprionate (2) in a first solvent and an acid to form a chiral ethyl(4-methoxyphenyl)-1-(α-methyl benzylamino)propionate (3). The formation of the chiral ethyl(4-methoxyphenyl)-1-(α-methyl benzylamino)propionate (3) occurs over a period of several hours to several days. Alternatively, the reaction mixture may be refluxed for several hours. Ethyl(4-methoxyphenyl)

-1-(α-methyl benzylamino)propionate (3) is then reacted with 3', 4'-methylenedioxy-2-nitrostyrene (4) with or without a second solvent, to form 2-(ethoxycarbonyl)-1-(4-anisyl)-3-piperonyl-4-nitrobutane 1-(α-methyl benzylamino) (5). 2-(ethoxycarbonyl)-1-(4-anisyl)-3-piperonyl-4-nitrobutane 1-(α-methyl benzylamino) (5) is then hydrolyzed to produce 2-(ethoxycarbonyl)-1-(4-anisyl)-3-piperonyl-4-nitrobutanone (6).

A base may be used to help the reaction of ethyl(4-methoxyphenyl)-1-(αmethyl benzylamino)propionate (3) with 3', 4'-methylenedioxy-2-nitrostyrene (4) in the presence of a second solvent to form the nitro enamine (5). Suitable bases for use in the reaction include, but are not intended to be limited to sodium ethoxide. Either (S) or (R) α-methyl benzylamine may be used to form the corresponding (S) or (R) ethyl(4-methoxyphenyl)-1-(α methylbenzylamino) propionate (3).

In another embodiment as shown in Scheme 2, an imino pyrolidine compound (7) is formed directly by hydrogenating 2-(ethoxycarbonyl)-1-(4-anisyl)-3-piperonyl-4-nitrobutane 1-(α-methyl benzylamino) (5) with hydrogen and a catalyst under pressure. Further hydrogenation of the imino pyrolidine compound (7) leads to the formation of 3-(ethoxycarbonyl)-2-(4-anisyl)-4-piperonylpyrollidine (8).

Hydrolysis of 2-(ethoxycarbonyl)-1-(4-anisyl)-3-piperonyl-4-nitrobutane 1-(α-methyl benzylamino) (5) to 2-(ethoxycabonyl)-1-(4-anisyl)-3-piperonyl-4-nitrobutanone (6) may be performed using an aqueous organic or an aqueous inorganic acid. Examples of suitable organic acids include, but are not intended to be limited to, acetic acid, citric acid, aspartic acid, benzoic acid, lactic acid, and succinic acid. Examples of suitable inorganic acids include, but are not intended to be limited to, hydrochloric acid, nitric acid, phosphoric acid, and sulfuric acid.

SCHEME 2

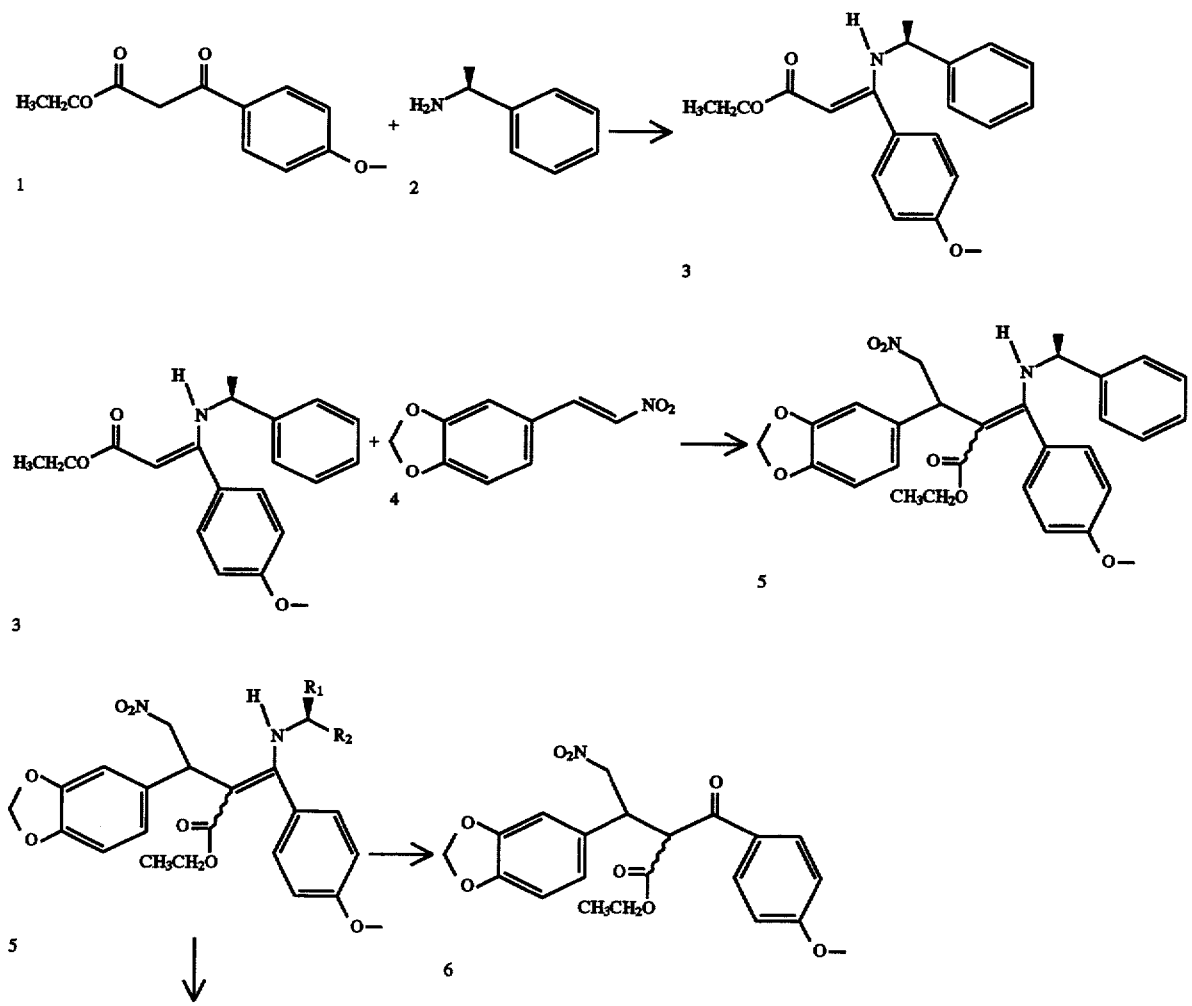

-continued
SCHEME 2

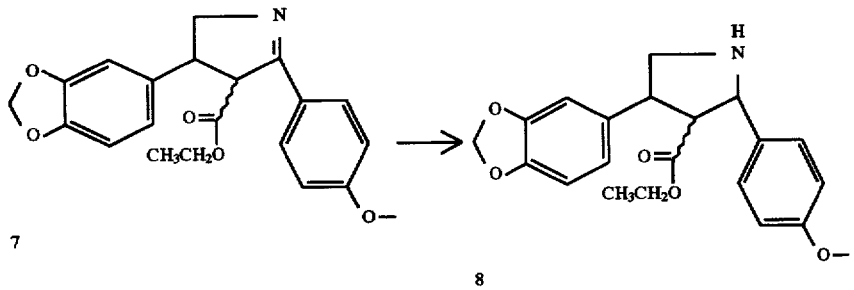

The following compounds were made in accordance with the process of the present invention. The Examples provided below are intended to be illustrative and not limiting of the present invention.

EXAMPLE 1
Ethyl(4-methoxyphenyl)-1-(α-methylbenzylamino) propionate (S) α-methylbenzylamine (0.6 grams (g), 5 millimoles (mmol)) and ethyl(4-methoxyphenyl)-1-oxo-proprionate were mixed in 1.8 g of tetrahydrofuran. Acetic acid (5 drops) was added to the mixture and the mixture was heated at reflux temperature for 10 hours. The reaction mixture was concentrated under vacuum and the resultant residue was purified using a on a silica gel column and eluting with 5–10% ethyl acetate in heptane to give 0.97 g of pure (S) ethyl(4-methoxyphenyl)-1-(α-methylbenzylamino) propionate, as confirmed by $^1$H-NMR. In the following examples, (R)ethyl (4-methoxyphenyl)-1-(α-methylbenzylamino)propionate was prepared in the same manner as the (S) isomer was prepared except that the (R) isomer was formed using (R) α-methylbenzylamine. $^1$NMR (400 MHz:CDCl$_3$) 1.3 (3H, t); 1.45 (3H, d); 3.8 (3H, s); 4.18 (2H, qd), 4.4–4.55 (1H, m); 4.6 (1H, m); 6.8–6.85(m, 2H); 7.1–7.3 (m, 5H).

EXAMPLE 2
2-(Ethoxycabonyl)-1-(4-Anisyl)-3-Piperonyl-4-Nitrobutanone (R) ethyl(4-methoxyphenyl)-1-(α-methyl benzylamino) propionate (500 milligrams (mg), 1.54 mmoles, 1.1 equivalents (equiv.)) and 3', 4'-methylenedioxy-2-nitrostyrene (270 mg, 1.40 mmoles; 1.0 equiv.) were combined in 5 milliliters (mLs) of ethanol and the reaction was stirred at room temperature for 3 days. Although the reaction was only 65% complete (formation of 2-(ethoxycarbonyl)-1-(4-anisyl)-3-piperonyl-4-nitrobutene 1-(α-methyl benzylamino) products) by HPLC analysis, the solution was hydrolyzed at 5° C. with 1.28 mL of 10% sulfuric acid (0.128 mL, 4.6 mmoles of H$_2$SO$_4$, 3 equiv.), and 0.5 mL of tetrahydrofuran (THF). After 16 hours, the sample showed less than 1% of unhydrolyzed enamino-ester. Diastereomeric 2-(ethoxycabonyl)-1-(4-anisyl)-3-piperonyl-4-nitrobutanone products were observed in pairs at approximately 26.8, 31.1, (first pair) and 38.0 and 57.5 minutes (second pair). The 2-(ethoxycabonyl)-1-(4-anisyl)-3-piperonyl-4-nitrobutanone products (first pair) was 23% in favor of the second peak. The 2-(ethoxycabonyl)-1-(4-anisyl)-3-piperonyl-4-nitrobutanone products (second pair) was 42% in favor of the third peak. $^1$NMR (400 MHz:CDCl$_3$) 1.14, 1.15 (2t,3H); 1.32, 1.33 (2d, 3H); 3.72, 3.73 (2s, 3H); 3.93–4.20 (m,4H); 4.70–4.95 (m, 2H); 5.81 (2s,2H0; 6.32–645 (m, 2H), 6.48–6.70 (m, 3H), 6.82–6.98 (m, 3H); 9.90, 9.93 (2 br d, 1H).

EXAMPLE 3
2-(ethoxycabonyl)-1-(4-anisyl)-3-piperonyl-4-nitrobutanone (R) Ethyl(4-methoxyphenyl)-1-(α-methyl benzylamino) propionate(500 mg, 1.54 mmoles, 1.1 equiv.) and 3', 4'-methylenedioxy-2-nitrostyrene(270 mg, 1.40 mmoles; 1.0 equiv.) were combined in 5 mLs ethanol and the heterogeneous reaction was brought to reflux. After 16 hours, HPLC analysis (Zorbax Rx-C8; 25 cm×4.6 mm; gradient elution from 30:70 to 70:30 Acetonitrile/water (0.1% phosphoric acid in 15 minutes; flow=1.5 mL/min; UV at 230 nm) indicated that the 3', 4'-methylenedioxy-2-nitrostyrene was nearly consumed so the solution was concentrated and chromatographed (SiO2, gradient eluent from heptane to 30% ethylacetate/heptane) producing 120 mg (0.23 mmoles) of 2-(ethoxycarbonyl)-1-(4-anisyl)-3-piperonyl-4-nitrobutene 1-(α-methyl benzylamino) diastereomers. To this sample was added 64 microliters (μL) of sulfuric acid (2.3 mmoles, 10 equiv.), 0.5 mL of water, 1 mL of ethanol and 0.5 mL of THF. After 16 hours, the sample showed less than 1% unhydrolyzed enamines so the solution was analyzed using a ChiralpakAS column (10% ethanol/hexane eluent, 1 mL/min; 254 nm). Diastereomeric 2-(ethoxycabonyl)-1-(4-anisyl)-3-piperonyl-4-nitrobutanone products were observed in pairs at.26.8, 31.1, (first pair) and 38.0 and 57.5 minutes (second pair). The 2-(ethoxycabonyl)-1-(4-anisyl)-3-piperonyl-4-nitrobutanone products (first pair) was 16% in favor of the second peak. The 2-(ethoxycabonyl)-1-(4-anisyl)-3-piperonyl-4-nitrobutanone (second pair) was 6% in favor of the fourth peak.

EXAMPLE 4
2-(ethoxycabonyl)-1-(4-anisyl)-3-piperonyl-4-nitrobutanone

A mixture of (S) ethyl(4-methoxyphenyl)-1-(α-methyl benzylamino) propionate (650 mg, 2.0 mmoles) and 3', 4'-methylenedioxy-2-nitrostyrene (380 mg, 2.0 mmoles) in ethanol (5 mL) was heated at 50 ° C. for 1 hour. HPLC analysis of the reaction mixture showed very little reaction. The mixture was heated at 65° C. for 40 minutes and still no reaction was observed. The mixture was then heated at reflux for 4.5 hours, after which the starting material had been consumed. The crude product was purified by flash chromatography (10% ETOAc/heptane) to give 470 mg of 2-(ethoxycarbonyl)-1-(4-anisyl)-3-piperonyl-4-nitrobutene 1-(α-methyl benzylamino) products (yellow oil). The 2-(ethoxycarbonyl)-1-(4-anisyl)-3-piperonyl-4-nitrobutene 1-(α-methyl benzylamino) products (203 mg, 0.319 mmoles) were mixed with ethanol (4 mL) and a solution of concentrated $H_2SO_4$ (35 μL, 0.66 mmoles) in water (4 mL) was added to the mixture. The resulting homogeneous solution was stirred at ambient temperature for 16 hours and HPLC analysis showed less than 1% of unhydrolyzed enamines. The solution was analyzed for the presence of 2-(ethoxycabonyl)-1-(4-anisyl)-3-piperonyl-4-nitrobutanone diastereomers using a ChiralPakAS column (90/10 hexane/ethanol; 1 mL/min; UV detection at 254 nm). 2-(ethoxycabonyl)-1-(4-anisyl)-3-piperonyl-4-nitrobutanone diastereomeric products were observed in pairs at 27.2, 31.7 (first pair) and 38.8 and 61.0 minutes (second pair). The 2-(ethoxycabonyl)-1-(4-anisyl)-3-piperonyl-4-nitrobutanone diastereomers of the first pair was 8% in favor of the first peak, and the 2-(ethoxycabonyl)-1-(4-anisyl)-3-piperonyl-4-nitrobutanone diastereomers of the second pair was 4% in favor of the third peak.

EXAMPLE 5

2-(ethoxycabonyl)-1-(4-anisyl)-3-piperonyl-4-nitrobutanone

A mixture of (S) ethyl(4-methoxyphenyl)-1-(α-methyl benzylamino) propionate (510 mg, 1.57 mmoles) and 3',4'-methylenedioxy-2-nitrostyrene (306 mg, 1.59 mmoles) in ethanol (5 mL) was stirred at room temperature for 72 hours. HPLC analysis indicated that approximately 50% of the reaction mixture proceeded to the formation of the 2-(ethoxycarbonyl)-1-(4-anisyl)-3-piperonyl-4-nitrobutene 1-(α-methyl benzylamino) products. The mixture was cooled in an ice-water bath and 10% $H_2SO_4$ (w/w) (4.6 grams (g), 4.71 mmoles) was added, resulting in the formation of an insoluble material. THF (0.5 mL) was added and the ice bath was removed to give a homogeneous solution that was stirred for 16 hours. HPLC analysis showed less than 1% of unhydrolyzed enamines and the presence of 2-(ethoxycabonyl)-1-(4-anisyl)-3-piperonyl-4-nitrobutanone diastereomers. Diastereomeric 2-(ethoxycabonyl)-1-(4-anisyl)-3-piperonyl-4-nitrobutanone products were observed in pairs at 27.6,32.2 (first pair) and 39.4 and 62.3 minutes (second pair).The 2-(ethoxycabonyl)-1-(4-anisyl)- 3-piperonyl-4-nitrobutanone products of the first pair was 54% in favor of the first peak and the 2-(ethoxycabonyl)-1-(4-anisyl)-3-piperonyl-4-nitrobutanone products of the second pair was 15% in favor of the fourth peak.

EXAMPLE 6

2-(ethoxycarbonyl)-1-(4-anisyl)-3-piperonyl-4-nitrobutene 1-(α-methyl benzylamino)

(S) ethyl(4-methoxyphenyl)-1-(α-methyl benzylamino) propionate (1.1 gm., 3.38 mmol) and 3',4'-methylenedioxy-2-nitrostyrene (850 mg, 4.4 mmol) were mixed and heated at 70° C. for 12 hours. The reaction (formation of 2-(ethoxycarbonyl)-1-(4-anisyl)-3-piperonyl-4-nitrobutene 1-(α-methyl benzylamino) products) was 90% complete by HPLC analysis. The ratio of the diastereomers was 3:1.

EXAMPLE 7

Cis, Cis-3-(ethoxycarbonyl)-2-(4-anisyl)-4-piperonylpyrollidine 2-(ethoxycarbonyl)-1-(4-anisyl)-3-piperonyl-4-nitrobutene 1-(α-methyl benzylamino) (3.0 g) in 20 mL of THF was mixed with acetic acid (346 mg) and Raney nickel (0.75 gm). The mixture was hydrogenated at 60 psi and 60° C. for 17.5 hours. Trifluoroacetic acid (1.86 gm) and Raney nickel (1.5 gm) were added and the hydrogenation reaction was continued for an additional 16 hours. Pyrolidine formation was confirmed by HPLC analysis. The reaction mixture was washed with distilled water (20 mL) and potassium carbonate (20 mL, 20%). The solvent was removed under a vacuum and the residue chromatographed to yield 2.0 gm of cis, cis-3-(ethoxycarbonyl)-2-(4-anisyl)-4-piperonylpyrollidine.

What is claimed:

1. A process for producing enhanced stereoselective nitro enamine diastereomers of the formula,

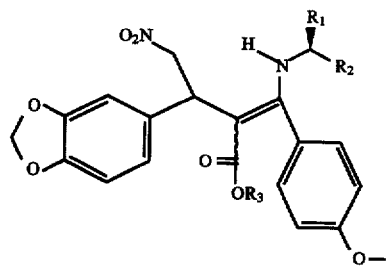

comprising the steps of:

(a.) reacting a chiral primary amine of the formula,

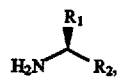

wherein $R_1$ and $R_2$ are independently selected from the group consisting of alkyl, substituted and unsubstituted aryl, heterocyclic, and alkoxy, with a -ketoester compound of the formula,

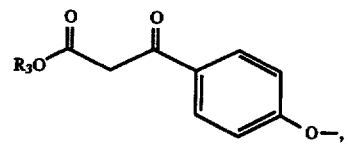

wherein $R_3$ is selected from the group consisting of alkyl and substituted and unsubstituted aryl, in the presence of a first solvent and an acid to form a chiral enamino-ester of the formula,

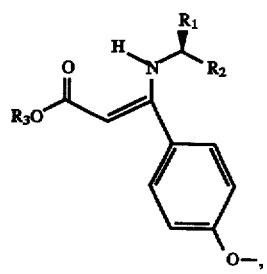

and (b.) reacting said chiral enamino-ester with a nitrostyrene compound of the formula,

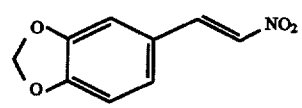

to form said nitro enamines diastereomers.

2. A process according to claim 1 wherein said first solvent is selected from the group consisting of: tetrahydrofuran, toluene and methyl tert-butyl ether.

3. A process according to claim 1 wherein said acid selected from the group consisting of: acetic, citric, aspartic, benzoic, lactic, sulphuric, and succinic acids.

4. A process according to claim 1 wherein a second solvent is used to react said chiral enamino-ester with said nitrostyrene compound to form said nitro enamines.

5. A process according to claim 4 wherein said second solvent is selected from the group consisting of: tetrahydrofuran (THF), alkanols, acetonitrile, methyl tert-butyl ether (MTBE), toluene, and ethyl acetate.

6. A process according to claim 1 wherein a base is added to step (b.).

7. A process according to claim 6 wherein said base is sodium ethoxide.

8. A process according to claim 1 wherein said nitro enamines are hydrolyzed to form nitro ketones of the formula,

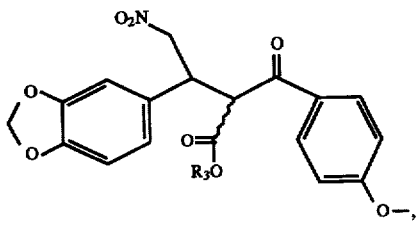

and its isomers.

9. A process according to claim 8 wherein said nitro enamines are hydrolyzed with an aqueous organic or an aqueous inorganic acid.

10. A process according to claim 9 wherein said aqueous organic acid is an aqueous solution of an organic acid selected from the group consisting of: acetic acid, citric acid, aspartic acid, benzoic acid, lactic acid, and succinic acid.

11. A process according to claim 10 wherein said aqueous inorganic acid is an aqueous solution of an inorganic acid selected from the group consisting of: hydrochloric acid, nitric acid, phosphoric acid, and sulfuric acid.

12. A process according to claim 1 wherein said primary amine is α-methyl benzylamine and said β-ketoester compound is ethyl(4-methoxyphenyl)-1-oxo-proprionate.

13. A process according to claim 1 wherein said enamino-ester is ethyl(4-methoxyphenyl)-1-(α-methylbenzylamino) propionate and said nitrostyrene compound is 3',4'-methylenedioxy-2-nitrostyrene.

14. A process according to claim 1 wherein said nitro enamines are hydrogenated to produce an imino pyrolidine compound of the formula,

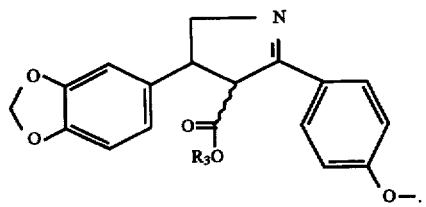

15. A process according to claim 14 wherein said imino pyrolidine compound is hydrogenated to produce a pyrolidine compound of the formula,

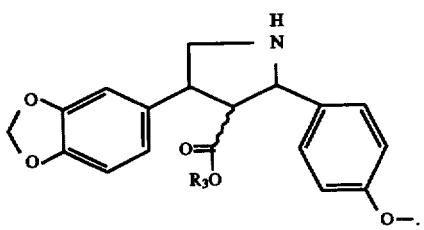

16. A process according to claim 14 wherein said hydrogenation is with hydrogen and a catalyst in an acid solution.

17. A process according to claim 1 wherein said nitro enamino products are 2(ethoxycarbonyl)-1-(4-anisyl)-3-piperonyl-4-nitrobutene 1-(α-methylbenzylamino) isomers.

18. A process according to claim 8 wherein said nitro ketone products are 2-(ethoxycarbonyl)-1-(4-anisyl)-3-piperonyl-4-nitrobutanone isomers.

19. A process according to claim 15 wherein said pyrolidine compound is cis, cis-3-(ethoxycarbonyl)-2-(4-anisyl)-4-piperonylpyrollidine.

* * * * *

UNITED STATES PATENT AND TRADEMARK OFFICE
CERTIFICATE OF CORRECTION

PATENT NO. : 5,801,250
DATED : September 1, 1998
INVENTOR(S) : Oliver-Shaffer et al.

It is certified that error appears in the above-identified patent and that said Letters Patent is hereby corrected as shown below:

Column 12, line 33, change "2(ethoxycarbonyl)" to --2-(ethoxycarbonyl)--.

Signed and Sealed this

Ninth Day of February, 1999

Attest:

Attesting Officer

Acting Commissioner of Patents and Trademarks